US009664627B2

(12) United States Patent
Horstmeyer

(10) Patent No.: US 9,664,627 B2
(45) Date of Patent: May 30, 2017

(54) METHOD AND DEVICE FOR THE ANALYSIS OF OILS AND TECHNICAL SERVICE FLUIDS AND FOR THE QUALIFIED EVALUATION OF THE OPERATING STATES OF UNITS

(71) Applicant: Gert Horstmeyer, Birstein (DE)

(72) Inventor: Gert Horstmeyer, Birstein (DE)

( * ) Notice: Subject to any disclaimer, the term of this patent is extended or adjusted under 35 U.S.C. 154(b) by 0 days.

(21) Appl. No.: 15/021,218

(22) PCT Filed: Sep. 11, 2014

(86) PCT No.: PCT/DE2014/100332
§ 371 (c)(1),
(2) Date: Mar. 10, 2016

(87) PCT Pub. No.: WO2015/035983
PCT Pub. Date: Mar. 19, 2015

(65) Prior Publication Data
US 2016/0223469 A1    Aug. 4, 2016

(30) Foreign Application Priority Data

Sep. 12, 2013 (DE) .......... 10 2013 110 011

(51) Int. Cl.
*G01N 33/28* (2006.01)
*G01N 21/94* (2006.01)
(Continued)

(52) U.S. Cl.
CPC ............. *G01N 21/94* (2013.01); *F16N 29/00* (2013.01); *F16N 39/00* (2013.01); *G01N 21/27* (2013.01);
(Continued)

(58) Field of Classification Search
CPC ...................................................... G01N 33/28
(Continued)

(56) References Cited

U.S. PATENT DOCUMENTS 4,781,892 A    11/1988    Dickakian
4,791,461 A  * 12/1988    Kishimoto .......... G01N 21/474
                                                    356/446
(Continued)

FOREIGN PATENT DOCUMENTS

DE        941520        4/1956
DE       19637234       3/1998
(Continued)

OTHER PUBLICATIONS

International Search Report for PCT/DE2014/100332, English Translation attached to original, Both completed by the European Patent Office on Jan. 9, 2015, All together 8 Pages.
(Continued)

*Primary Examiner* — Roy M Punnoose
(74) *Attorney, Agent, or Firm* — Brooks Kushman P.C.

(57) ABSTRACT

A method and device for analyzing oils, technical service fluids and for the evaluation of the operating states of units, wherein a drop of test fluid to be examined is applied to a test medium which is allowed to penetrate the medium, and is evaluated after a preselected time by optically comparing a resulting image with the data of a plurality of reference images with respect to a plurality of test criteria. The test fluids to be examined can give information about the state of the test fluids. Fast and reliable detection, evaluation, and assessment are possible and reduce the influence of subjective assessment influences. A computer-assisted comparison of the data of the images with the data of the reference images is performed. Data of the images from the front, back-light, and possibly the UV back-light recording are associated with images for a test criterion that has the greatest correspondence.

18 Claims, 3 Drawing Sheets

(51) Int. Cl.
*F16N 29/00* (2006.01)
*F16N 39/00* (2006.01)
*G01N 21/27* (2006.01)

(52) U.S. Cl.
CPC ......... *G01N 33/28* (2013.01); *G01N 33/2835* (2013.01); *G01N 33/2888* (2013.01); *F16N 2200/04* (2013.01); *F16N 2250/34* (2013.01); *F16N 2270/50* (2013.01); *G01N 2201/061* (2013.01)

(58) Field of Classification Search
USPC .......................................................... 356/70
See application file for complete search history.

(56) References Cited

U.S. PATENT DOCUMENTS

| | | | |
|---|---|---|---|
| 5,091,652 A | 2/1992 | Mathies et al. | |
| 5,313,824 A | 5/1994 | Herguth et al. | |
| 5,846,837 A * | 12/1998 | Thym | G01N 33/521 422/423 |
| 6,598,464 B1 | 7/2003 | Rossi | |
| 7,449,903 B2 | 11/2008 | Huebner | |
| 8,748,185 B2 | 6/2014 | Horstmeyer | |
| 9,329,128 B2 * | 5/2016 | Petrich | B01L 3/5027 |
| 9,329,159 B2 * | 5/2016 | Walicki | G01N 31/22 |
| 2007/0236234 A1 | 10/2007 | Huebner | |

FOREIGN PATENT DOCUMENTS

| | | |
|---|---|---|
| DE | 102005058595 | 7/2006 |
| DE | 102005015826 | 10/2006 |
| EP | 0571295 | 11/1993 |
| EP | 0635714 | 1/1995 |
| EP | 0711999 | 5/1996 |
| EP | 1825256 | 2/2010 |
| WO | 2009080049 | 7/2009 |

OTHER PUBLICATIONS

Gerardo Trujillo, Practicing Oil Analysis Jul. 1, 2003, Retrieved on Mar. 29, 2016, XP 055161107, 4 Pages, "The Blotter Spot Method, Sample Preparation and Test Procedure, A Quick Guide". Http://www.machinerylubrication.com/Articles/Print/499.

* cited by examiner

US 9,664,627 B2

METHOD AND DEVICE FOR THE ANALYSIS OF OILS AND TECHNICAL SERVICE FLUIDS AND FOR THE QUALIFIED EVALUATION OF THE OPERATING STATES OF UNITS

CROSS-REFERENCE TO RELATED APPLICATION

This application is the U.S. national phase of PCT Application No. PCT/DE2014/100332 filed on Sep. 11, 2014, which claims priority to DE Patent Application No. 10 2013 110 011.2 filed on Sep. 12, 2013, the disclosures of which are incorporated in their entirety by reference herein.

TECHNICAL FIELD

The invention relates to a method and a device for the analysis of oils and technical service fluids and for the qualified evaluation of the operating states of units, wherein a drop of the test fluid to be examined is applied to a suitable test medium, is allowed to penetrate into the test medium and is assessed after a preselected time by a resulting test image being optically compared with the data of a plurality of reference images according to a plurality of test criteria.

BACKGROUND

The method and the associated device can be used to examine different test fluids with regard to various features, contents and contamination, for example engine oils, hydraulic oils, transmission oils, brake fluids, industrial oils and cooking, baking and foodstuff oils.

The invention serves for analyzing possible damage as a result of normal or unusual wear and imminent damage in units appertaining to the automotive industry such as, for example, engines, brakes, power steering systems or transmissions and in installations, gear mechanisms, hydraulic mechanisms and controllers of industrial installations by means of the analysis of the corresponding oils or service fluids. Moreover, it serves for analyzing the quality of oils and service fluids in industry, for example the food industry, especially in kitchens.

DE 941 520 B describes a device for testing lubricating oil or similar substances with regard to an amount of foreign or discoloring constituents contained therein with the aid of an absorption spot on an absorbent paper. According to the invention, this aim is achieved by virtue of the fact that the greater portion of a sheet of paper, at its surface, e.g. by means of a color coating, is embodied such that it is comparatively non-absorbent or even repellent with respect to the substance to be tested, or the oil, and a plurality of comparatively absorbent locations are recessed in said portion, said locations having markings in the comparison color in their interior. The color comparison between a respective absorbent sample applied to a respective non-absorbent location and the associated marking for different samples is then intended to be able to be carried out very easily.

U.S. Pat. No. 5,313,824 A describes a test kit and a manual method for the analysis of lubricating oil in which a sample is applied on a test medium for a specific time and can be subjected to a visual comparison with a sample.

DE 10 2005 058 595 A1 and EP 1 825 256 B1 describe a test medium and a method for the rapid analysis of engine oils in internal combustion engines. There a drop of an oil to be examined is applied to a specific test medium and allowed to penetrate into the test medium. After a predefined time, a person carries out a manual assessment in such a way that the resulting image is visually compared with a plurality of reference images.

In the previous visual assessment by the eye of an observer, the results of the tests can be individually evaluated differently. Moreover, human eyes see very differently and perceive colorations differently. This constitutes a degree of uncertainty. Moreover, not all constituents are detected by the eye. Certain constituents in the oils to be examined cannot be identified by the eye. The method of visual assessment by the eye is only a broad-brush approach. The evaluation by the user is subject to a number of subjective influences and is learnable only with a relatively great effort in terms of practice. Human inertia also plays a part here, which often takes a critical stance toward new things. The previous methods require explanation and are training-intensive. In borderline cases the evaluation of the results is not reliable enough.

U.S. Pat. No. 5,091,652 A relates to a fluorescence scanner and more particularly to a scanner that scans gel excited to fluorescence by a laser, comprising a confocal microscope detection system.

DE 10 2005 015 826 A1 describes a method and a system for the optical inspection of contact pads on semiconductor components having different appearances. The position of contact needle tips on a contact pad can be determined by a procedure in which a first image of the surface of the contact pad is recorded before the contacting of the contact pad, a second image of said surface is recorded after the contacting of the contact pad by a contact element, and a third image is generated from the formation of the difference between the first and second images, said third image being analyzed in order to ascertain at what location the contact needle left an impression on the contact pad.

Neither of the aforementioned solutions is suitable for analyzing oils and other technical service fluids and allowing conclusions to be drawn about units from which they were taken.

EP 0 571 295 A1 describes a device for evaluating a lubricant, more particularly for a motor vehicle engine, in which a front light recording is created and is automatically assessed with regard to specific lubricant properties.

A method described in DE 196 37 234 A1 serves for online checking of the color purity of surfaces by means of a device consisting of one or a plurality of video cameras and a computer, in particular for the purpose of quality control.

U.S. Pat. No. 4,781,892 A describes an apparatus and a method for determining the fouling tendency of liquid hydrocarbons in which a front recording in the form of reflected light and a back light recording in the form of transmitted light are created. An assessment is carried out by means of the light intensity.

It is an object of the invention to propose a method and a device for the analysis of oils and technical service fluids in which the test fluids to be examined can themselves give information about the state of said test fluids and statements and evaluations regarding the mechanical-technical state of the components and units associated with the test fluids can be made. The invention is intended to afford a possibility of rapid and reliable detection, assessment and evaluation. The influence of subjective evaluation influences is intended to be reduced or completely excluded.

SUMMARY

The invention achieves the object by means of the features specified in the claims. Advantageous developments of the invention are specified in the dependent claims and are explained in greater detail below together with the described embodiments of the invention, including the drawings.

The method for the analysis of oils and technical service fluids and for the qualified evaluation of the operating states of units is based on the fact that a drop of the test fluid to be examined is applied to a suitable test medium, that said drop penetrates into the test medium and an image that can be assessed results after a specific time. This test image is optically compared with the data of a plurality of reference images according to specific test criteria.

As a preparatory measure, series of reference images for different test criteria are recorded and stored as data. These reference images are assigned to specific properties of the fluids to be examined and operating states of units, such that a specific state is assigned to each reference image.

For the actual analysis, the test image of the drop that forms on the test medium is recorded by an image recording apparatus at least in a front recording and a back light recording and is stored. In one particular embodiment, the back light recording can be a UV light recording. In one preferred embodiment, a UV back light recording can be carried out in addition to the back light recording using white and/or colored light. A computer-aided comparison of the data of the test images with the data of the reference images is subsequently carried out by the data of one or a plurality of images from the front, the back light and, if appropriate, the UV back light recording being assigned to the reference images for a respective test criterion which has the greatest correspondence. This is followed by display and/or logging of the properties of the test fluid and/or of the operating state of the unit which correspond to the assigned data of the reference images.

Since the individual test fluids to be examined have very different properties and the state of the different units from which the test fluids were taken, such as, for example, brake, power steering, transmission or hydraulically controlled installations or components such as power steering systems, can also be influenced by very different criteria, for each test medium and for each unit a dedicated series of reference images should be created and taken as a basis for the analysis. Once these reference images have been created, they can repeatedly be taken as a basis for the analysis and assessment. In this regard, it also becomes possible that new test fluids or units can be integrated into the analysis system very simply and rapidly.

The computer-aided comparison of the data of the test images with the data of the reference images is preferably carried out by means of software suitable for differentiating the shape and/or the color spectra of the data of the test images and the data of the reference images and for assigning the data of the images from the front, the back light and, if appropriate, the UV back light recording to a respective reference image for a respective test criterion.

The recording and storage of the data of the reference images can be carried out on an internal computer or on an external server. In the case of external storage, the computer-aided comparison can also be carried out on the external server, in which case there must then be a connection from the test image recording apparatus, for example a USB connection or an online connection.

Differently colored light sources can be used for the front recording and/or the back light recording, which light sources can improve the assessment of the resulting test images for specific test criteria. The image recording apparatus itself can also contain photographic filters, for example specific color or neutral filters.

In regard to the actual test recordings, the image recording apparatus creates a recording for identification and documentation for an assignment of the test fluid to a sampling, for example type of test fluid, time of recording, and/or an object, for example a specific vehicle, and/or a person, for example a client. By way of example, a front recording can also be used for this purpose.

Various suitable coated or uncoated carrier materials such as filter or laboratory paper, plastics films, aluminum foils can be used as the test medium. In one preferred embodiment, a test medium is used, having a weight per unit area of 50.0 g/m$^2$ to 200.0 g/m$^2$, comprising, relative to the total weight of the test medium, 70.0% by weight to 98.0% by weight of cotton pulp, 0.0% by weight to 25.0% by weight of cellulose and 0.5% by weight to 30.0% by weight of silicic acid and/or at least one silicate.

The method described is suitable for examining the test fluids with regard to various test criteria. A number of variants are possible for obtaining a test result that can be assessed. In this regard, each individual recording from the front, the back light and, if appropriate, the UV back light recording can be compared with in each case a series of reference recordings for in each case only one test criterion, or a recording is examined and assessed with a plurality of series of reference recordings with regard to equally a plurality of test criteria.

Test criteria may be, for example, in the case of engines, the soot content, metal proportions or sediments, the state of the engine oil itself, its aging, additive degradation or the content of condensation water or cooling water or of fuel; in the case of brakes, abrasion, dirt ingress, the water content or the additive degradation (sludge settlement); in the case of power steering systems, the abrasion, the dirt ingress or the additive degradation and, in the case of transmissions, metal abrasion or water ingress by cooling water, for example in automatic transmissions.

For the analysis of the state of health a unit, test fluid can be examined with regard to contained contaminants resulting from soot, dust, metal abrasion by a procedure in which a soot spot that arises in the center of the test image in a region a is compared with the data of the reference images and the content of contaminants is determined and evaluated.

For the analysis of the state of health of units, test fluid can be examined with regard to the state of the test fluid by a procedure in which an annulus that arises in a region b of the test image is compared, with regards to its color, with the data of the reference images and the quality of the test fluid in relation to its aging, for example the oil running performance, is determined and evaluated.

A further possibility consists in the fact that for the analysis of the state of health of units, test fluid can be examined with regard to the content of water and/or cooling fluid, for example glycol, present in the water by a procedure in which a jagged edge zone that arises in a region c of the test image is compared, with regard to its shape, with the data of the reference images and the water content of the test fluid in relation to the state of the unit is determined and evaluated.

For the analysis of the state of health of units, test fluid can be examined with regard to the content of fuel by a procedure in which a fuel circle that arises at the outer ring of the test image in a region d is compared, with regard to its shape and color, with the data of the reference images and the fuel content of the test fluid in relation to the state of the unit is determined and evaluated.

The device according to the invention for the analysis of oils and technical service fluids and for the qualified evaluation of the operating states of units comprises a support or a mount for a planar test medium, for example a carrier plate. A drop of the test fluid to be examined can be applied on the test medium and a test image can be created. The support should be clear or at least light-transmissive in order to make possible and not falsify back light recordings.

For recording the test images, the device has at least one image recording apparatus for a front recording and a back light recording and at least in each case one light source for image acquisition for a front recording and a back light recording. The image recording apparatus may be a camera or an optical-digital scanner, for example a laser scanner. In each case one or a plurality of image recording apparatuses can be present or a plurality of different image recording apparatuses can be combined with one another. In one particular embodiment, the back light recording can be a UV back light recording. In one preferred embodiment, in regard to a back light recording using preferably normal light, an additional UV back light recording can be carried out. For both variants, it is necessary to provide corresponding light sources for image acquisition for the UV back light recording.

The device furthermore includes means for storing the test image that forms on the test medium, and means for storing the data of a plurality of series of reference images. The means for storing the test image that forms on the test medium are, in particular, an internal data memory linked to a computer. The image recording apparatus can also contain the customary image memories, at least for temporary storage. The means for storing the data of a plurality of series of reference images are situated as data memories either in an internal computer or an external server with customary equipment such as processors, data memories, power supplies and associated drivers and software.

Furthermore, the device include means, in particular software, suitable for comparing the data of the test images with regard to their shape and color spectra with the data of the reference images and for assigning the data of in each case one image or a plurality of images from the front, the back light and, if appropriate, the UV back light recording to in each case one reference image or reference images for a respective test criterion which has the greatest correspondence. Said software can be situated either on an internal computer or on an external server, depending on where the assessment is intended to be carried out.

Finally, the device has a display unit and/or a logging unit for representing and/or outputting the analysis and/or evaluation results.

The support, the image recording apparatuses, the light sources and, if appropriate, the display unit and/or the logging unit are preferably situated within a housing, which should be protected against external influences. The support or the mount for the test medium can have an additional locking element which positions the planar test medium always at a specific location, in order that comparable recordings can be created. In addition, provision can be made of a protection device for protection against soiling of the recording apparatuses, the light sources or the test medium, e.g. additional glass plates.

One particular embodiment of the invention relates to a device in which the actual test recording apparatus has an interface to a network and/or to the internet and the means for storing the data of a plurality of series of reference images and also the software for the comparison and the assignment of the data of the test images with the data of the reference images are situated on an external server. The device can then be operated as a client server apparatus via an online connection.

It is furthermore possible for the test recording apparatus to serve only for recording the data of the test images and, if appropriate, the reference images and for the storage to be carried out on a directly connected computer, from which a connection is then made, if appropriate, to an external server on which the assessment takes place. The display, logging or outputting of the test results can then be carried out either on the test recording apparatus itself or on the directly connected computer.

The device can thus be a stationary apparatus, a mobile terminal having a dedicated power supply or a combination of the two.

The advantages of the present invention reside in the fact that the optical-electronic method affords more certainty in the detection and assessment. Different interpretations, such as with the human eye, are precluded to the greatest possible extent. The method is faster and more precise since the constituents in the oils can be determined more accurately and significantly more accurate evaluations will be present as a result. The examination of the components and units becomes much more accurate as a result of this method, and the statements become better founded. That leads to better results in these test methods. The invention likewise affords further advantages in the representation, communication and archiving of the test results.

The invention enables an indirect examination of the state of engines and units, without having to open or dismantle them.

BRIEF DESCRIPTION OF THE DRAWINGS

The invention is explained in greater detail below on the basis of an exemplary embodiment. In the figures.

DETAILED DESCRIPTION

Figure 1:
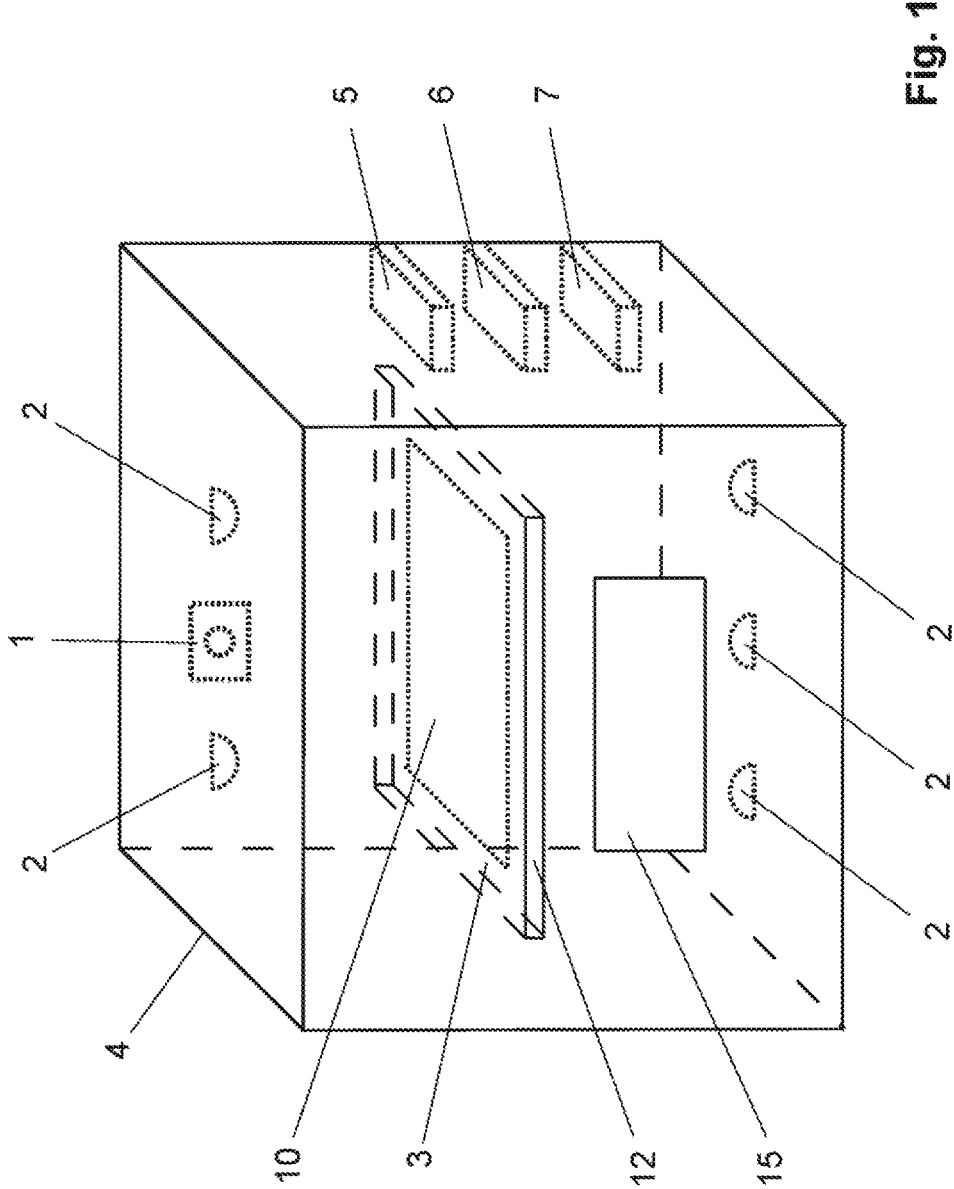
FIG. 1 shows a device with image acquisition by a camera system

One exemplary device is illustrated in FIG. 1. It shows a device for the analysis of oils and technical service fluids and for the qualified evaluation of the operating states of units, with an optical-electronic image acquisition by a camera system.

A sealed housing 4 has a receptacle slot 12 for inserting a sheet of a test medium 10, to which a drop of the test fluid to be examined can be applied and a test image can be created. Situated behind the receptacle slot 12 is a support for the test medium 10, said support being embodied as a glass carrier plate 3. A camera 1 is fixed above the carrier plate 3 with the test medium 10, said camera being suitable for creating a plurality of front, backlit and UV back light recordings and for storing them in a computer 5. Two light sources 2 for front recordings are fitted alongside the camera 1. Three further light sources 2 are provided below the carrier plate 3, wherein the left light source 2 generates white light, the middle light source 2 generates UV light and the right light source 2 generates yellow light. The white light and the yellow light are provided for back light recordings and the UV light is provided for UV back light recordings.

In the present example, the data of a plurality of series of reference images are stored internally in the same memory of the computer 5 where the test images are also stored. The computer 5 contains software suitable for comparing the data of the test images with regard to their shape and color spectra with the data of the reference images and for assigning the data of in each case one image or a plurality of images from the front, the back light and the UV back light recording to in each case one reference image or reference images for a respective test criterion which has the greatest correspondence. As a result of this assessment, the analysis and evaluation results are logged on one of the data memories present, for example the computer 16, and are displayed on the display unit 15. The computer 5 also contains the software for controlling the sequential steps for creating the test images.

The housing 4 of the test recording apparatus also contains an energy connection 6 and an interface 7 for external connections, for example a USB connection for external storage possibilities or for outputting the results. In addition, the interface 7 can contain a network card for an internet connection.

Figure 2:
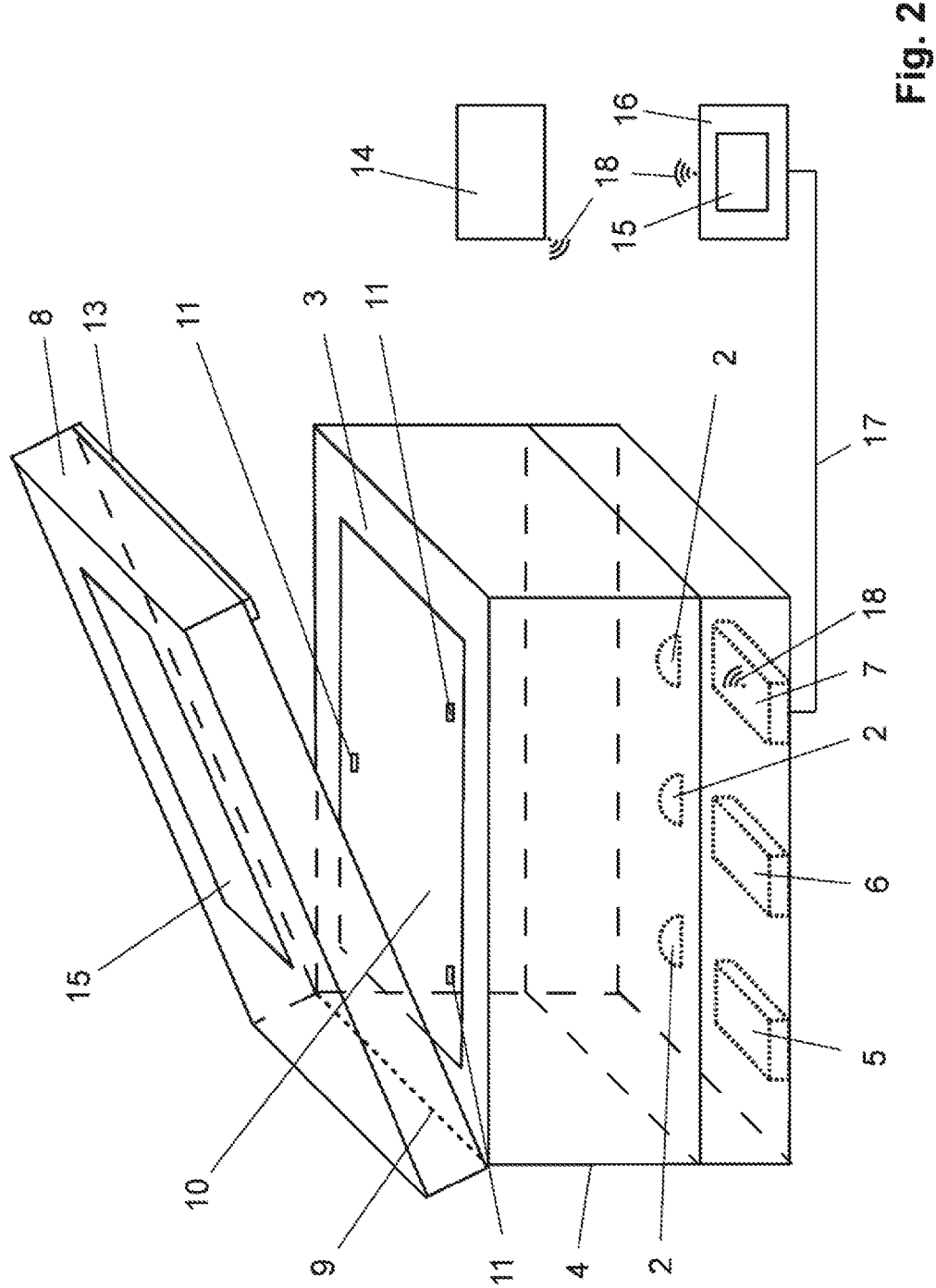
FIG. 2 shows a device with scanner and hinged cover

FIG. 2 illustrates a further example. Instead of a receptacle slot, here the sheet of a test medium 10 having the drop of the test fluid to be examined is received directly on a glass carrier plate 3. Three locking holes are recessed in the test medium 10 and correspond to the 3 locking elements 11 on the carrier plate 3, such that the test medium 10 can be fixed precisely in said locking elements 11 and comparable conditions always prevail during the image acquisition.

Before the test images are created by means of a scanner unit 13 serving as an image recording apparatus, the cover 8 hinged about a hinge 9 is closed. Depending on whether the scanner is arranged below or above the test medium, either front or back light recordings can be carried out. In addition, the housing contains even further light sources 2, for example for UV or color recordings.

Adapted flatbed scanners having a movable carriage can be used for recording and digitizing the test images or the reference images. In the case of flatbed scanners, the test media to be scanned are placed onto an original glass, illuminated by a fluorescence or halogen light source and protected against the ambient brightness by a cover 8. In this case, opaque originals are illuminated from below and transparent originals are illuminated from above by a transmitted-light unit. The light source, the entire optical assembly and the CCD sensors are mounted on a carriage that is moved away in the longitudinal direction continuously below the original. The reflected light is directed with the aid of two mirrors and a synchronously focusing lens unit onto a straight series of thousands of CCD sensors and is digitized in full width in successive lines. The transmitted-light unit is mounted instead of the covering and contains a lamp that is moved in parallel with the carriage over the original and illuminates the latter from above in the process.

The recording apparatus can also be provided with a removable cover instead of with a receptacle slot 12 or with a hinged cover 8.

The processing and assessment are carried out in a manner similar to that in the example according to FIG. 1, except that the reference images and the software for the assessment are not arranged within the housing of the test recording apparatus, but rather on an external server 14, and the device is operated as a client server apparatus via a radio connection 18.

In preparation, various series of reference images are created for different test fluids. Since diesel and gasoline engines yield different images, for example, these should also be assessed separately. Gas-operated and biodiesel-operated engines can also be assessed.

The manner of functioning will be explained below on the basis of an example illustrated in FIG. 3, in which a drop of an engine oil of a diesel engine is intended to be analyzed.

For the example described here, the engine oil is intended to be assessed according to 4 different test criteria I to IV. In the 4 illustrations on the left lying below another, FIG. 3 shows what images form as a result of the drop being dripped onto the test medium 10 and what regions of the images are assessed according to specific criteria. The meaning of the images that arise is explained below.

Test Criterion I—Soot Formation and Contamination by Dust, Metal Abrasion, Etc.

The inner circle indicates in a region a soot formation and contamination by dust, metal abrasion, etc. Depending on the combustion state of the engine and abrasion or dust possibly present, a soot spot arises. If the oil has already undergone very many kilometers of running in the engine, the circles 2 and 3 may even be covered by soot. A "healthy" engine having an oil running performance of 5000 or 10 000 km exhibits the rings distinctly. For this test criterion, a test series in 9 different test states is established and stored as reference images for a later computer-aided comparison on a central server. The reference image series comprising the 9 reference images for test criterion I is illustrated on the right in FIG. 3.

Test Criterion II—State of the Engine Oil

The second circle indicates in a region b the state of the engine oil. The following holds true in the case of gasoline engines: the older the oil, the darker brown it becomes, and in the case of diesel engines from light gray to deep black. If an engine undergoes very severe soot formation, there is often no discernible difference between the circles 1 and 2. If the oil is still all right, but the engine undergoes severe soot formation, a further light circle forms around the brown (in the case of diesel black) spot in the center, said circle thus indicating the state of the engine oil as all right. For this test criterion, a test series in 9 different test states is established and stored as reference images for a later computer-aided comparison on a central server. The reference image series comprising the 9 reference images for test criterion II is illustrated on the right in FIG. 3.

Test Criterion III—Water in the Oil

The jagged edge zone c (arrow) around the second circle shows water in the oil. The test fluid then begins to form jags at the edges immediately after the drawing in of the oil. If there is a large amount of water in the oil, this is recognized after just a few minutes. With high water content, the results of 1, 2 and 4 can be superimposed. Two types of water are differentiated: condensation water and cooling water (comprising glycol). Both form jags at the edge. If there is glycol in the engine oil, this is recognized after about ½ hour on the basis of the outer, yellow ring ("corona") around the jagged rim, which becomes steadily larger and more distinct. For this test criterion, a test series in 3 different test states is established and stored as reference images for a later computer-aided comparison on a central server. The reference image series comprising the 3 reference images for test criterion III is illustrated on the right in FIG. 3.

Test Criterion IV—Fuel in the Oil

The outer ring d forms the fuel circle. If there is fuel in the oil, then a light, transparent ring forms around the outside. The larger the ring becomes, the more fuel there is in the oil (arrow). A light ring will always form—the larger the latter in relation to the drop, the more fuel is present. If a ring becomes discernible after a few hours, then that should be classified as "medium" and all right. For this test criterion, a test series in 3 different test states is established and stored as reference images for a later computer-aided comparison on a central server. The reference image series comprising the 3 reference images for test criterion IV is illustrated on the right in FIG. 3.

The actual analysis method can then be carried out. A drop of the engine oil to be examined is applied to a planar test medium. The test medium measuring approximately 50 mm×50 mm consists, by way of example, of a carrier material having a weight per unit area of 140 g/m², relative to the total weight of the test medium. It consists of 100% by weight of cotton pulp and 0% by weight of cellulose. The test medium is coated with specific substances as catalyst, accelerator and reactant.

After a penetration time of from approximately 0.15 to 45 min (depending on the loading of the oil) and a curing time of 1-8 hours, the resultant image can be assessed. For this purpose, the test medium is inserted into the slot provided for it in the test recording apparatus or, as in FIG. 2, is placed onto the carrier plate 3 and fixed by means of 3 locking elements 11. The test recording apparatus is switched on and a front, a back light and a UV back light recording are created by means of the contained camera 1 and light sources and are stored digitally in the computer 16 connected by means of a USB connection 17.

The operator of the test recording apparatus is then requested to start the assessment. In this case, the test images are transmitted to the external server 14 over the internet via the interface 7 contained in the test recording apparatus or in the connected computer 16, the reference images already having been stored on said external server.

The external server 14 contains software suitable for comparing the data of the test images with regard to their shape and color spectra with the data of the reference images and for assigning the data of in each case one image or a plurality of images from the front, the back light and the UV back light recording to in each case one reference image or reference images for a respective test criterion. The resulting test image is then compared with the data of a plurality of reference images according to a plurality of test criteria in the server. In this case, the software determines, for each of the 4 test criteria, with what reference image the respective test image has the greatest correspondence.

Since a specific test result was assigned to each reference image or to a plurality of reference images, following the decision as to which of the reference images is closest to the test image, it is also possible to indicate what properties are to be assigned to the respective test image.

There are various possibilities for assessing test images. In principle, there is the possibility of assessing a test image according to a plurality of criteria. It has proved to be advantageous if a plurality of recordings are created and, for specific test criteria, particularly suitable recordings are also selected from the front, the back light or the UV back light recording. For the recording and assessment of test criteria I and II mentioned above, a front recording is widely sufficient in many cases. Moreover, the front recording is used to create and document an identification and assignment to the respective test. The back light recording is used, in particular, for identification and assessment of test criteria 3 and 4. The use of colored light makes it possible to support the assessment in specific color spectra. The UV back light recording is carried out, in particular, for the spectral color assessment of the inner circle according to test criterion 1 and of the state of the engine oil according to test criterion 2. As back light recording, the UV back light recording is also additionally suitable for clarifying the presence of condensation water or cooling water according to test criterion 3 and the presence of fuel according to test criterion 4.

Figure 3:
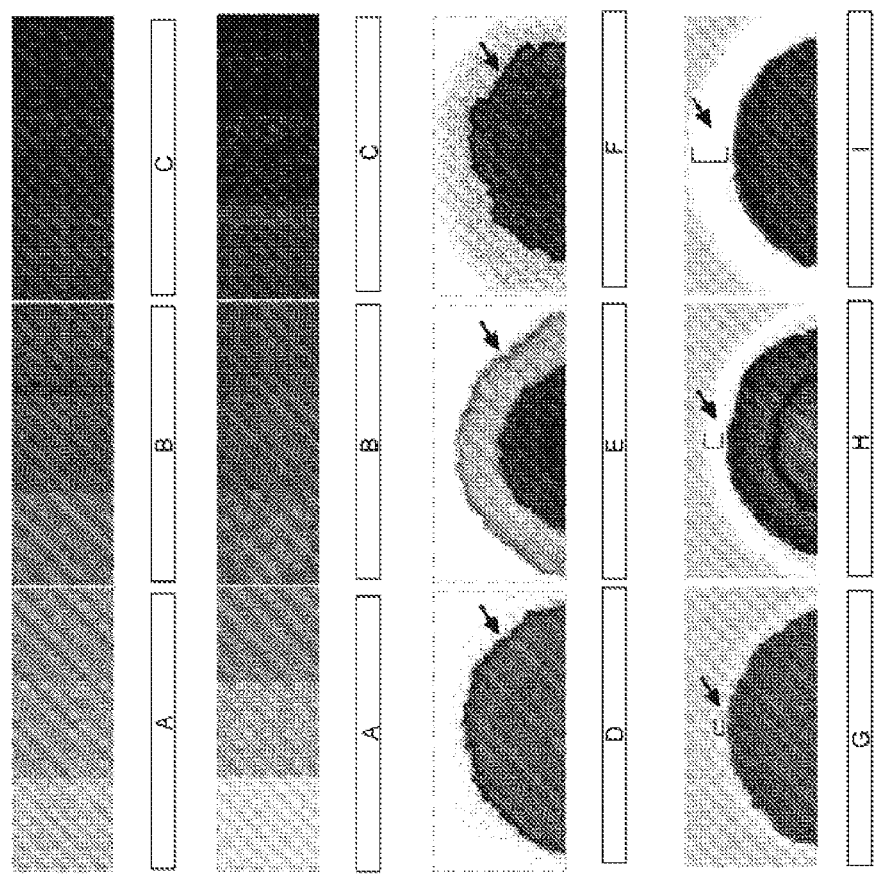
FIG. 3 shows an illustration of four test criteria and of four series with reference images
Figure 3:
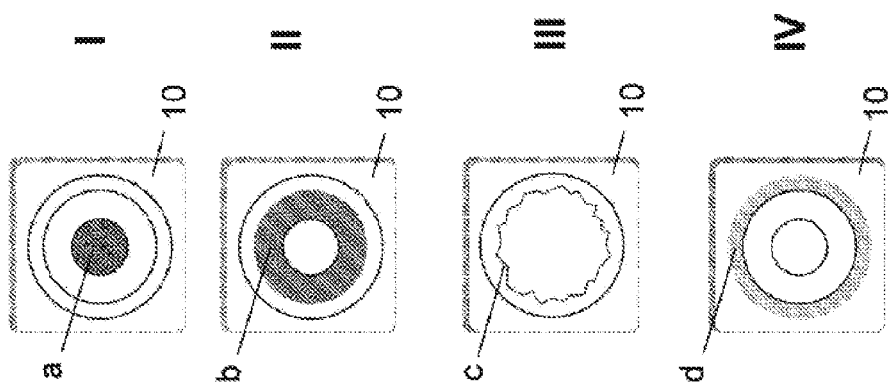

The present example according to FIG. 3 illustrates how four test images are examined and evaluated according to a respective test criterion. A test medium 10 having a drop of engine oil of a diesel engine is illustrated on the left in the top row I in FIG. 3.

The test results in the reference images according to FIG. 3 have the following meanings:

Row I: soot and contaminants (combustion residues)

Range A: the test result in this range means that the engine does not contain elevated soot and/or dirt portions.

Range B: elevated soot and dirt formation is present in the engine. It is recommended that a specialist workshop be visited within the foreseeable future in order to enable a more accurate diagnosis to be performed.

Range C: it is recommended that a specialist workshop be visited urgently starting from range C of the scale.

The causes of poor results may be incomplete combustion, poor setting of the carburetor, incorrect way of driving, deficient injection, clogged full flow filter, faults at the exhaust or turbocharger. The consequences would be a possible build-up of soot on valves and the pistons lead to impaired heat exchange. Increased wear and fuel consumption and worsened emission values arise as a result.

Row II: state of the engine oil (oxidation and aging of the engine oil)

Range A: the tested oil is in a good state.

Range B: with such a test result, the oil exhibits first aging phenomena. The running performance of the oil should also be taken into consideration. A low running performance in conjunction with pronounced oil aging indicates possible damage.

Range C: a timely oil change is recommended.

The causes of a poor test result indicate an excessively long change interval, momentary overheating, incorrect oil or an excessively high sulfur content of the fuel. The consequences might be that spent engine oil leads to higher wear on piston rings and engine parts. This results in higher consumption values in conjunction with decreasing engine performance.

Row III: water in the oil (condensation water or cooling water, glycol)

Range D: there is no water in the oil.

Range E: the oil contains a slightly to moderately elevated proportion of water. It is recommended that a renewed test be conducted within the next 1000 km and that a specialist workshop be visited in the event of deterioration.

Range F: there is too much water in the oil.

Causes of too much water in the oil might be that water passes into the oil circuit through faulty seals, porous oil cooler seals, defective cylinder head seal, cracks in the cooling water circuit or corroding soldered joints on the oil cooler.

Consequences: this can lead to considerable engine damage. It is recommended that a specialist workshop be visited urgently.

Row IV: fuel in the oil (combustion state as a result of fuel dilution)

Range G: an elevated proportion of fuel cannot be detected in the oil.

Range H: the oil contains a slightly to moderately elevated proportion of fuel. Dilution of the oil and impaired lubrication properties can already occur.

Range I: unburnt fuel moves past the piston into the engine oil.

Causes of fuel in the engine oil may be deficient injection, an incorrect setting of the carburetor, ignition or the valve control. The injection nozzles or the piston rings may also be defective. The consequences are deficient lubrication properties as a result of dilution of the oil, a risk of overheating, increased wear, high fuel consumption or poor emission values. It is recommended that a specialist workshop be visited urgently.

After assessment has been carried out in the external server 14, the test results are communicated to the test recording apparatus or to the computer 16—for example a laptop—connected to the test recording apparatus by means of a USB connection 17. The properties of the engine oil and the respective assigned operating states of the diesel engine are displayed and/or logged on the display unit 15 and/or the logging unit on the test recording apparatus or on the connected computer 16.

The tester receives a printed analysis of the "state of health" of said tester's engine and can initiate the recommended measures.

LIST OF REFERENCE SIGNS

1 Camera
2 Light source
3 Support (carrier plate)
4 Housing
5 Computer
6 Energy connection
7 Interface
8 Cover
9 Hinge
10 Test medium
11 Locking element
12 Receptacle slot
13 Scanner unit
14 External server
15 Display unit
16 Computer
17 USB connection
18 Radio connection
A Good
B Medium
C Poor
D No water in the oil
E Some water in the oil
F Large amount of water in the oil
G No fuel in the oil
H Some fuel in the oil
I Large amount of fuel in the oil

The invention claimed is:

1. A method for the analysis of oils and technical service fluids and for the qualified evaluation of the operating states of units, wherein a drop of a fluid to be examined is applied to a test medium, is allowed to penetrate into the test medium and is assessed after a preselected time by a resulting test image being optically compared with data of a plurality of reference images according to a plurality of test criteria, comprising the following method steps:

recording and storage of the data of a plurality of series of reference images for different test criteria and assignment of the reference images to specific properties of the fluids to be examined and operating states of units, recording and storage of the test image of the drop that forms on the test medium using an image recording apparatus at least in a front light recording and a back light recording, computer-aided comparison of the data of the test images with the data of the reference images and assignment of the data of one or a plurality of images from the front light and the back light recording to the reference images for a respective test criterion which has the greatest correspondence, and display and/or logging of the properties of the fluid to be examined and/or of an operating state of the unit which correspond to the assigned data of the reference images.

2. The method as claimed in claim 1, wherein a recording and storage of the test image of the drop that forms on the test medium is carried out by the image recording apparatus by way of a UV back light recording.

3. The method as claimed in claim 1, wherein the computer-aided comparison is carried out by software for differentiating shape and/or color spectra of the data of the test images and the data of the reference images and for assigning the data of the images from the front light and the back light recording to the reference images for a respective test criterion.

4. The method as claimed in claim 1, wherein the recording and storage of the data of the reference images is carried out on an external server, and in that the computer-aided comparison is carried out on the external server, to which an online connection is possible.

5. The method as claimed in claim 1, wherein differently colored light sources are used for the front light recording and/or the back light recording.

6. The method as claimed in claim 1, wherein the image recording apparatus creates a recording for identification and documentation for an assignment of the fluid be examined to a sampling and/or an object and/or a person.

7. The method as claimed in claim 1, wherein a test medium is used, having a weight per unit area of 50.0 g/m$^2$ to 200.0 g/m$^2$, comprising, relative to a total weight of the test medium, 70.0% by weight to 98.0% by weight of cotton pulp, 0.0% by weight to 25.0% by weight of cellulose and 0.5% by weight to 30.0% by weight of silicic acid and/or at least one silicate.

8. The method as claimed in claim 1, wherein for analysis of the state of health of units, the fluid to be examined, is examined with regard to contained contaminants resulting from soot, dust, metal abrasion by a procedure in which a soot spot that arises in the center of the test image in a region a is compared with the data of the reference images and the content of contaminants is determined and evaluated.

9. The method as claimed in claim 1, wherein for the analysis of the state of health of units, fluid to be examined is examined with regard to the state of the test fluid by a procedure in which an annulus that arises in a region b of the test image is compared, with regards to its color, with the data of the reference images and quality of the fluid to be examined in relation to its aging, for example the oil running performance, is determined and evaluated.

10. The method as claimed in claim 1, wherein for the analysis of the state of health of units, fluid to be examined is examined with regard to the content of water and/or cooling fluid (e.g. glycol) present in the water by a procedure in which a jagged edge zone that arises in a region c of the test image is compared, with regard to its shape, with the data of the reference images and water content of the fluid to be examined in relation to the state of the unit is determined and evaluated.

11. The method as claimed in claim 1, wherein for the analysis of the state of health of units, fluid to be examined is examined with regard to the content of fuel by a procedure in which a fuel circle that arises at the outer ring of the test image in a region d is compared, with regard to its shape and color, with the data of the reference images and the fuel content of the fluid to be examined in relation to the state of the unit is determined and evaluated.

12. A device for the analysis of oils and technical service fluids and for the qualified evaluation of the operating states of units for carrying out a method as claimed in claim 1, comprising:
- a support for a planar test medium, to which a drop of the fluid to be examined can be applied and a test image can be created,
- at least one image recording apparatus for a front light recording and a back light recording,
- at least in each case one light source for image acquisition for the front light recording and a back light recording,
- means for storing data of a plurality of series of reference images,
- means for storing a test image that forms on the test medium,
- software for comparing the data of the test image with regard to its shape and color spectra with the data of the reference images and for assigning the data of in each case one image or a plurality of images from the front light and the back light recording to in each case one reference image or reference images for a respective test criterion which has the greatest correspondence, and
- a display unit and/or a logging unit for representing and/or outputting the analysis and/or evaluation results.

13. The device as claimed in claim 12, wherein a light source for a UV back light recording is present and the image recording apparatus is capable of acquiring a UV back light recording.

14. The device as claimed in claim 12, wherein the image recording apparatus is a digital camera.

15. The device as claimed in claim 12, wherein the image recording apparatus is a scanner unit having an optical-digital scanner, for example a laser scanner.

16. The device as claimed in claim 12, wherein the device has an interface to a network and/or an internet access, and the storage for storing the data of a plurality of series of reference images and also the software for the comparison and the assignment of the data of the test images with the data of the reference images are situated on an external server to which an online connection is possible and the device can be operated as a client server apparatus.

17. The device as claimed in claim 12, wherein the device comprises a mobile terminal having a dedicated power supply.

18. The device as claimed in claim 12, further comprising a receptacle for the planar test medium having a locking element for fixing the test medium.

* * * * *